United States Patent
Anderson et al.

(10) Patent No.: US 9,302,269 B2
(45) Date of Patent: Apr. 5, 2016

(54) SEED SAMPLING APPARATUS AND METHOD

(75) Inventors: Edwin J Anderson, Dallas Center, IA (US); Steven M Becker, Johnston, IA (US); Thomas G Lade, Ankeny, IA (US); Kenneth J Ross, Des Moines, IA (US)

(73) Assignee: PIONEER HI-BRED INTERNATIONAL INC., Johnston, IA (US)

( * ) Notice: Subject to any disclaimer, the term of this patent is extended or adjusted under 35 U.S.C. 154(b) by 298 days.

(21) Appl. No.: 14/233,506

(22) PCT Filed: Jul. 16, 2012

(86) PCT No.: PCT/US2012/046858
§ 371 (c)(1),
(2), (4) Date: Jan. 17, 2014

(87) PCT Pub. No.: WO2013/012778
PCT Pub. Date: Jan. 24, 2013

(65) Prior Publication Data
US 2014/0166786 A1    Jun. 19, 2014

Related U.S. Application Data

(60) Provisional application No. 61/508,935, filed on Jul. 18, 2011.

(51) Int. Cl.
*B02C 18/16* (2006.01)
*G01N 1/28* (2006.01)
(Continued)

(52) U.S. Cl.
CPC ............. *B02C 18/16* (2013.01); *B02C 23/08* (2013.01); *B02C 23/18* (2013.01); *G01N 1/286* (2013.01); *G01N 33/0098* (2013.01); *G01N 1/20* (2013.01); *G01N 2001/2021* (2013.01)

(58) Field of Classification Search
CPC ........ B02C 18/16; B02C 23/18; B02C 23/08; B02C 9/04; B02C 13/288; B02C 13/00; G01N 33/0098; G01N 1/286; G01N 1/20; G01N 2001/2021
USPC .................. 241/6–13, 19, 79.1, 101.8, 25
See application file for complete search history.

(56) References Cited

U.S. PATENT DOCUMENTS

| | | |
|---|---|---|
| 2007/0207485 A1 | 9/2007 | Deppermann et al. |
| 2008/0131924 A1 | 6/2008 | Cope et al. |
| 2011/0062256 A1 | 3/2011 | Cope et al. |

FOREIGN PATENT DOCUMENTS

| | | |
|---|---|---|
| WO | 2008103609 A1 | 8/2008 |
| WO | 2008150798 A1 | 12/2008 |
| WO | 2010108082 A1 | 9/2010 |

OTHER PUBLICATIONS

PCT International Search Report dated Nov. 2, 2012; International Patent Application No. PCT/US2012/046858.
(Continued)

*Primary Examiner* — Mark Rosenbaum
(74) *Attorney, Agent, or Firm* — Pioneer Hi-Bred Int'l, Inc.

(57) ABSTRACT

An apparatus (100) configured to simultaneously sample a plurality of seeds is provided. The apparatus (100) may include a grinder (110) configured to grind each of the seeds of a first plurality of seeds to produce a powder comprising a plurality of seed particles. A sample container (142) may be configured to receive the powder. Further, a cleaning device may be configured to introduce a neutral media to the grinder (110) to substantially prevent cross-contamination with a second plurality of seeds, which may be ground thereafter. The apparatus (100) may further comprise a mixing device (150) configured to mix the powder. Thereby a sample portion of the powder may be tested for the presence of a genetically modified organism, or other tests may be conducted thereon. A related method for high throughput simultaneous sampling of a plurality of seeds is also provided.

14 Claims, 9 Drawing Sheets

(51) Int. Cl.
*B02C 23/08* (2006.01)
*B02C 23/18* (2006.01)
*G01N 33/00* (2006.01)
*G01N 1/20* (2006.01)

(56) References Cited

OTHER PUBLICATIONS

PCT International Preliminary Report on Patentability dated Jan. 21, 2014; International Patent Application No. PCT/US2012/046858.

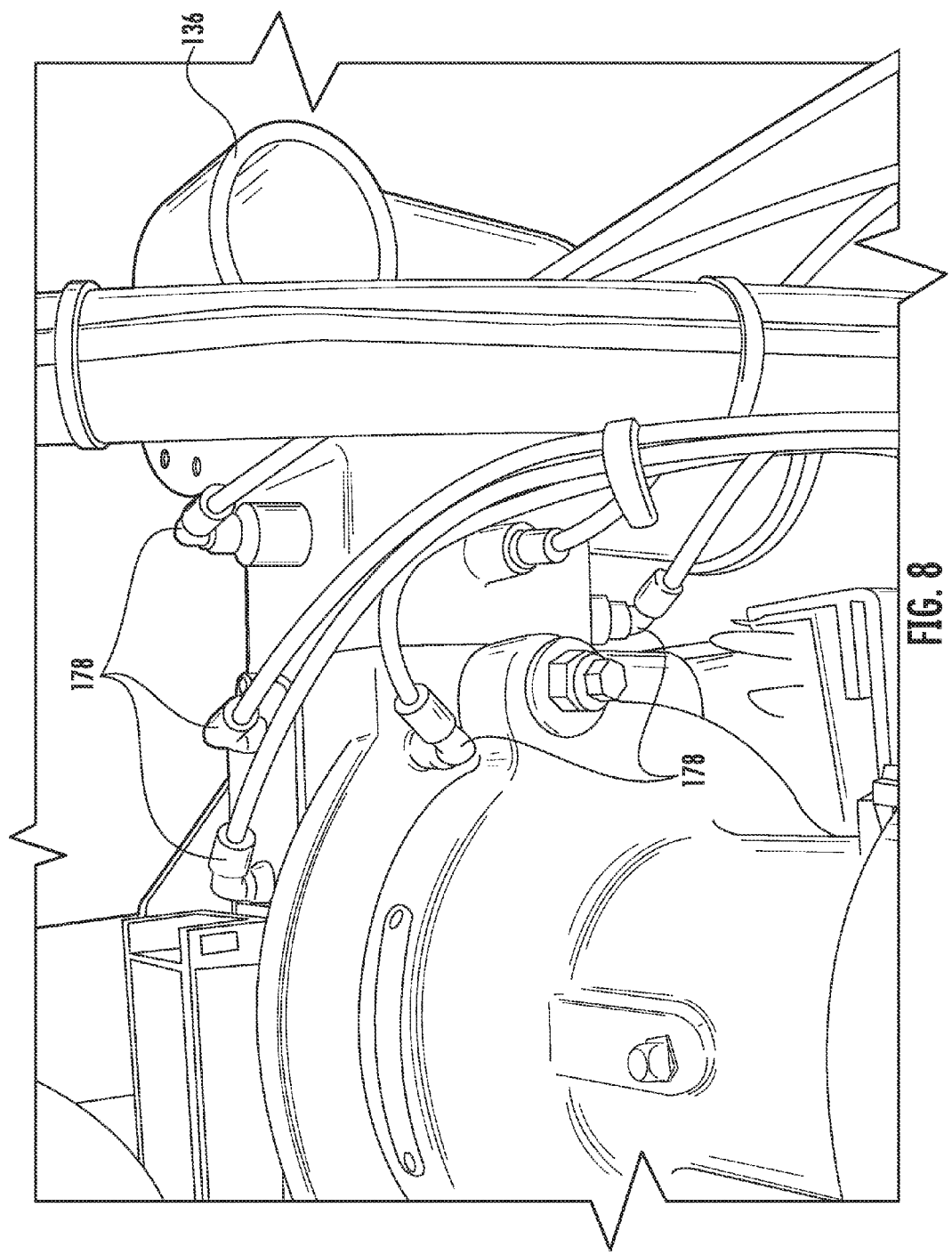

```
                  ┌──────────────────────────────────────────────┐
                  │ RECEIVE A FIRST PLURALITY OF SEEDS IN A HOPPER │──200
                  └──────────────────────────────────────────────┘
                                      │
                  ┌──────────────────────────────────────────────┐
                  │    METER THE FIRST PLURALITY OF SEEDS INTO   │──202
                  │                  A GRINDER                    │
                  └──────────────────────────────────────────────┘
                                      │
       ┌────────────────────────────────────────────────────────────────┐
       │ GRIND EACH OF THE SEEDS OF THE FIRST PLURALITY OF SEEDS IN THE │──204
       │ GRINDER TO PRODUCE A POWDER COMPRISING A PLURALITY OF SEED      │
       │ PARTICLES                                                       │
       └────────────────────────────────────────────────────────────────┘
                                      │
       ┌────────────────────────────────────────────────────────────────┐
       │ REGULATE A MAXIMUM DIMENSION OF THE SEED PARTICLES EXITING THE │──214
       │ GRINDER                                                         │
       └────────────────────────────────────────────────────────────────┘
                                      │
              ┌──────────────────────────────────────────────┐
              │     DIRECT A FLUID FLOW THROUGH THE GRINDER   │──216
              │           WHILE GRINDING THE SEEDS            │
              └──────────────────────────────────────────────┘
                                      │
              ┌──────────────────────────────────────────────┐
              │   SEPARATE THE SEED PARTICLES FROM THE FLUID  │──218
              │        FLOW USING A CYCLONE SEPARATOR         │
              └──────────────────────────────────────────────┘
                                      │
                  ┌──────────────────────────────────────────┐
                  │   COLLECT THE POWDER IN A SAMPLE CONTAINER │──206
                  └──────────────────────────────────────────┘
                                      │
                       ┌──────────────────────────────────┐
                       │     SEAL THE SAMPLE CONTAINER     │──220
                       └──────────────────────────────────┘
                                      │
                  ┌──────────────────────────────────────────┐
                  │     MIX THE POWDER IN THE SAMPLE CONTAINER │──222
                  └──────────────────────────────────────────┘
                                      │
                       ┌──────────────────────────────────┐
                       │      TUMBLE THE SAMPLE CONTAINER   │──224
                       └──────────────────────────────────┘
                                      │
     ┌───────────────────────────────────────────────────────────────────┐
     │ MIX THE POWDER TO OBTAIN A SUBSTANTIALLY HOMOGENEOUS DISTRIBUTION │──226
     │ OF THE SEED PARTICLES FROM THE SEEDS WITHIN THE POWDER            │
     └───────────────────────────────────────────────────────────────────┘
                                      │
                  ┌──────────────────────────────────────────┐
                  │    SELECT A SAMPLE PORTION OF THE POWDER  │──208
                  │                FOR TESTING                 │
                  └──────────────────────────────────────────┘
                                      │
              ┌──────────────────────────────────────────────┐
              │   TEST FOR PRESENCE OF A GENETICALLY MODIFIED │──228
              │          ORGANISM IN THE SAMPLE PORTION        │
              └──────────────────────────────────────────────┘
                                      │
              ┌──────────────────────────────────────────────┐
              │    DIRECT AN AMBIENT AIR FLOW GENERALLY DOWN  │──230
              │              AND AWAY FROM THE GRINDER        │
              └──────────────────────────────────────────────┘
                                      │
                  ┌──────────────────────────────────────────┐
                  │   DISTRIBUTE A NEUTRAL MEDIA INTO THE GRINDER │──210
                  └──────────────────────────────────────────┘
                                      │
     ┌───────────────────────────────────────────────────────────────────┐
     │ GRIND THE NEUTRAL MEDIA TO SUBSTANTIALLY PREVENT CROSS-CONTAMINATION│──212
     │             WITH A SECOND PLURALITY OF SEEDS                       │
     └───────────────────────────────────────────────────────────────────┘
                                      │
              ┌──────────────────────────────────────────────┐
              │  PROJECT A CLEANING MIXTURE INTO THE CYCLONE  │──232
              │   SEPARATOR TO CLEAN THE CYCLONE SEPARATOR    │
              └──────────────────────────────────────────────┘
                                      │
              ┌──────────────────────────────────────────────┐
              │  DIRECT A PRESSURIZED FLOW OF AIR INTO THE    │──234
              │         GRINDER TO CLEAN THE GRINDER          │
              └──────────────────────────────────────────────┘
```

FIG. 9

SEED SAMPLING APPARATUS AND METHOD

FIELD OF THE INVENTION

Various embodiments of the present invention relate generally to an apparatus and method for sampling seeds. More specifically, embodiments of the present invention provide an apparatus and method configured to simultaneously sample a plurality of seeds while substantially preventing cross-contamination.

BACKGROUND OF THE INVENTION

In the production of seed, testing may be required to determine the purity of the seed or other attributes thereof. For example, various rules and regulations may prohibit the inclusion of genetically modified organisms ("GMOs") in seed sold for agricultural purposes. Accordingly, the seed may need to be tested to verify compliance with the rules and regulations.

However, individually sampling seeds is virtually impossible given the vast numbers of seeds which may be distributed to farmers. Thus, simultaneous sampling of seeds by processing the seeds and testing the seeds at the same time may represent a viable alternative to individually sampling seeds. However, while bulk sampling may overcome issues with respect to processing large quantities of seed, additional issues may arise.

BRIEF SUMMARY

In one embodiment a method for high throughput simultaneous sampling of a plurality of seeds is provided. The method may include receiving a first plurality of seeds in a hopper, metering the first plurality of seeds into a grinder, and grinding each of the seeds of the first plurality of seeds in the grinder to produce a powder comprising a plurality of seed particles. The method may further include collecting the powder in a sample container and selecting a sample portion of the powder for testing. Additionally, the method may include distributing a neutral media into the grinder and grinding the neutral media to substantially prevent cross-contamination with a second plurality of seeds.

In some embodiments the method may further comprise regulating a maximum dimension of the seed particles exiting the grinder. Also, the method may include mixing the powder to obtain a substantially homogeneous distribution of the seed particles from the seeds within the powder. Additionally, the method may comprise sealing the sample container and mixing the powder in the sample container. Further, the method may include tumbling the sample container.

In some embodiments the method may also comprise directing a fluid flow through the grinder while grinding the seeds and separating the seed particles from the fluid flow using a cyclone separator. Additionally, the method may include projecting a cleaning mixture into the cyclone separator to clean the cyclone separator. The cleaning mixture may comprise the neutral media in some embodiments. Also, the neutral media may comprise a granulated plastic material or a plurality of control seeds which do not comprise a genetically modified organism in some embodiments. Additionally, in some embodiments grinding the neutral media may be conducted prior to grinding the seeds of the first plurality of seeds.

In some embodiments the method may additionally comprise directing an ambient air flow generally down and away from the grinder. Further, the method may include directing a pressurized flow of air into the grinder to clean the grinder. Also, the method may comprise testing for presence of a genetically modified organism in the sample portion.

In an additional embodiment an apparatus configured to simultaneously sample a plurality of seeds is provided. The apparatus may include a grinder configured to grind each of the seeds of a first plurality of seeds to produce a powder comprising a plurality of seed particles. A sample container may be configured to receive the powder. Further, a cleaning system may be configured to introduce a neutral media to the grinder to substantially prevent cross-contamination with a second plurality of seeds.

In some embodiments the apparatus may further comprise a control unit configured to maintain a substantially constant load on a motor driving the grinder. Further, a cyclone separator may be configured to separate the seed particles from a fluid flow. The cleaning system may be configured to project a cleaning mixture into the cyclone separator to clean the cyclone separator. The apparatus may additionally include a mixing device configured to mix the powder to obtain a substantially homogeneous distribution of the seed particles from the seeds within the powder. Also, a lid may be configured to seal the sample container, wherein the mixing device is configured to tumble the sample container while the sample container is sealed.

In some embodiments the apparatus may further include a metering device configured to meter the seeds into the grinder. Additionally, a screen may be configured to regulate a maximum dimension of the seed particles exiting the grinder. The cleaning system may comprise one or more air jets configured to direct a pressurized flow of air into the grinder to clean the grinder. Additionally, a negative air flow system may be configured to direct an ambient air flow generally down and away from the grinder. Also, in some embodiments the sample container may be further configured to store the first plurality of seeds before the first plurality of seeds are ground into the powder.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 8 illustrates an enlarged rear view of air jets of the apparatus of FIG. 1 in accordance with an example embodiment of the present invention; and FIG. 9 illustrates a method for high throughput simultaneous sampling of a plurality of seeds in accordance with an example embodiment of the present invention.

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
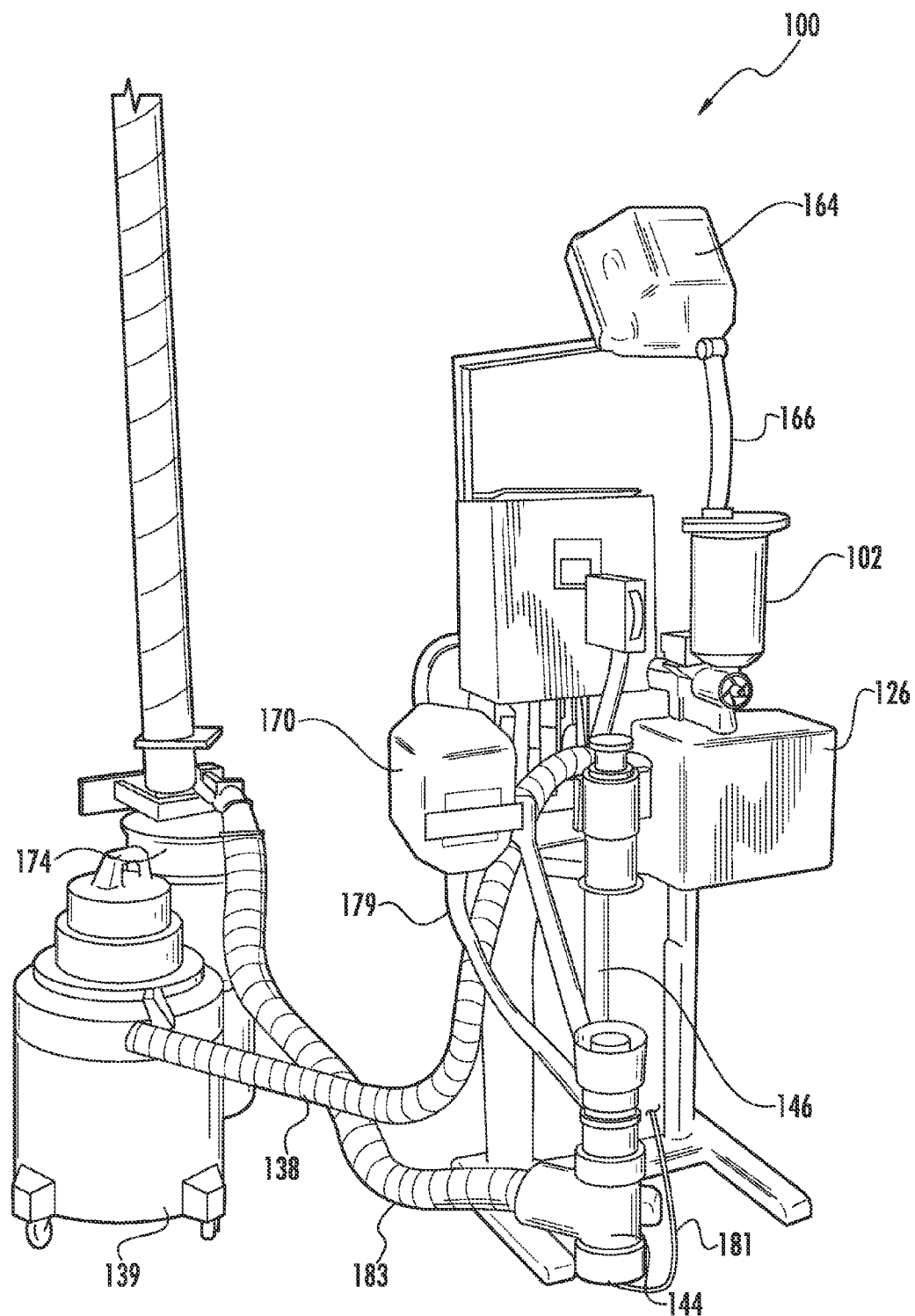
FIG. 1 illustrates an embodiment of an apparatus configured to simultaneously sample a plurality of seeds in accordance with an example embodiment of the present invention.
Figure 2:
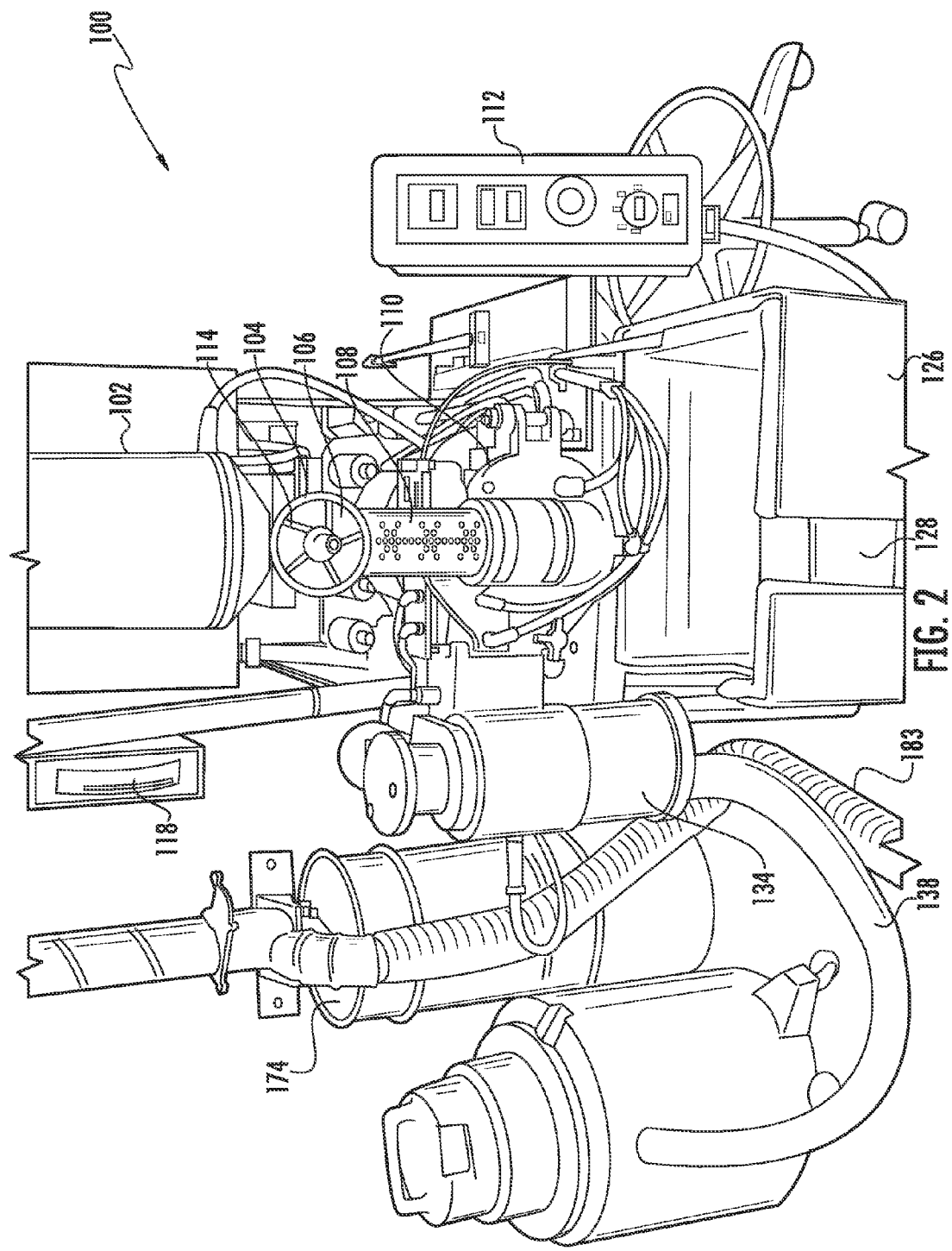
FIG. 2 illustrates an enlarged view of a seed hopper and grinder of the apparatus of FIG. 1 in accordance with an example embodiment of the present invention.

One embodiment of an apparatus 100 configured to simultaneously sample a plurality of seeds is illustrated in FIG. 1. The apparatus 100 may comprise a seed hopper 102 configured to receive and hold seeds which are to be sampled. The seed hopper 102 may comprise a translucent or transparent material such as glass or plastic which allows an operator to view the seeds within the seed hopper. As illustrated in FIG. 2, the seed hopper 102 may be coupled to a metering device 104. The metering device 104 may comprise a viewing panel 106 on the front which may also be formed from a translucent or transparent material such as glass or plastic.

In this regard, the metering device 104 may be configured to meter the seeds through a connecting tube 108 to a grinder 110. Use of a transparent or translucent seed hopper 102 and viewing panel 106 on the metering device 104 may allow the operator to view the seeds and know when all of the seeds from the seed hopper have been metered through the metering device to the grinder 110. In some embodiments of the apparatus 100 the metering device 104 may be hand operated. For example the user may rotate a crank to operate the metering device 104 and meter the seeds into the grinder 110 at a desired rate. However, the illustrated embodiment the apparatus 100 comprises a control unit 112 which may be configured to control the metering device 104 and meter the seeds into the grinder 110 at a desired rate. The metering device 104 may comprise a plurality of paddles 114 between which the seeds fall from the seed hopper 102 when the metering device is rotated. Thereby, relatively consistent quantities of the seeds may be delivered to the grinder 110 from between the paddles 114 as the metering device 104 rotates.

Figure 3:
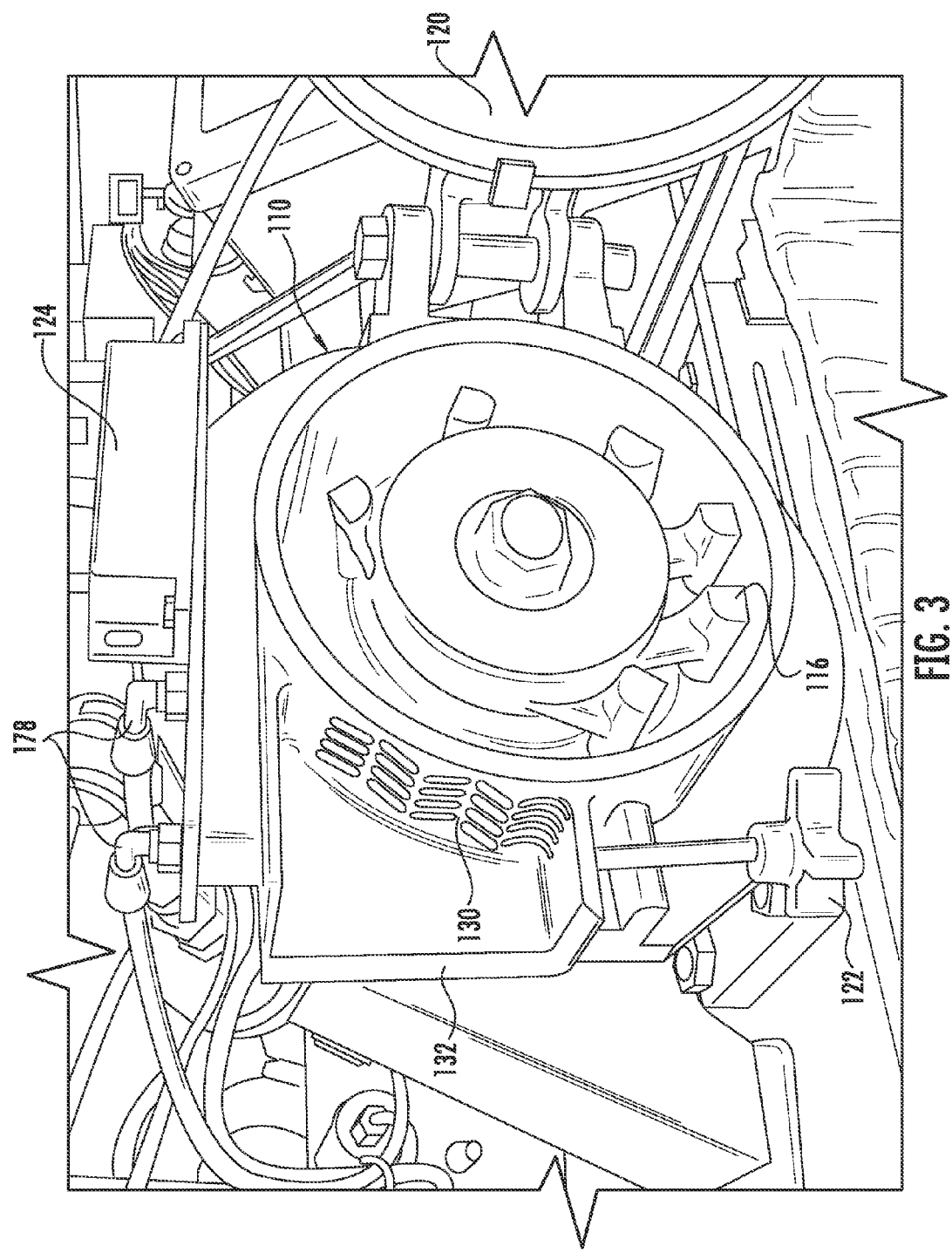
FIG. 3 illustrates an enlarged view of the inside of the grinder illustrated in FIG. 2 in accordance with an example embodiment of the present invention.

One embodiment of the grinder 110 is illustrated in FIG. 3. The illustrated embodiment of the grinder 110 comprises a hammer mill grinder, although various other embodiments of grinders may be employed in alternate embodiments of the apparatus 100 as would be understood by one having skill in the art. The grinder 110 may comprise a plurality of hammers 116 which rotate and swing as the grinder operates. Thereby, the hammers 116 grind the seeds which are delivered to the grinder 110 by the metering device 104.

As noted above, the metering device 104 meters the seeds into the grinder 110. Metering the seeds into the grinder 110 may be employed to control the amount of seeds which are in the grinder at any one time. For example, the grinder 110 may have a limited capacity which limits the number of seeds which may be received. Further, the grinder 110 may have to exert additional effort when more seeds are received.

In this regard, as illustrated in FIG. 2, the apparatus 100 may comprise an amperage gauge 118 which outputs an amperage reading corresponding to the load on a motor driving the grinder 110. In embodiments employing a hand crank or other embodiment of a manual metering device, the operator may view the reading on the amperage gauge 118 to determine when and/or at what rate to meter seeds into the grinder 110. For example, the operator may attempt to maintain a constant amperage reading and/or prevent the amperage reading from exceeding a threshold value.

In embodiments wherein the control unit 112 controls the metering device, the control unit may receive a signal from the amperage gauge 118 indicating the amperage draw by the motor and thereby the control unit may automatically maintain a constant amperage draw and/or prevent the amperage draw from exceeding a threshold value. Accordingly, by maintaining a substantially constant load on the motor, as reflected by a substantially constant amperage draw, the longevity of the motor driving the grinder 110 may be increased and the seeds may be ground more consistently.

Returning to FIG. 3, it should be noted that the grinder 110 is illustrated with a grinder door 120 in an open configuration. However, the grinder door 120 will normally be closed during operation. In this regard, the grinder door 120 may retain the seeds within the grinder 110 and prevent the seeds from spilling out of the grinder and also prevent access to the hammers 116 during operation, which may otherwise present a safety hazard. Accordingly, the grinder 110 may further comprise a locking mechanism 122 which may secure the grinder door 120 in a closed configuration (see, e.g., FIG. 2), whereby the grinder door is substantially locked in place. However, to further ensure that the grinder door 120 is fully closed prior to and during operation, the apparatus 100 may additionally comprise a safety switch 124. The safety switch 124 may be configured to detect whether or not the grinder door 120 is in the closed configuration and output a signal indicating whether the grinder door is in the closed configuration. Accordingly, the control unit 112 may be configured to prevent and/or stop operation of the grinder 110 in the event that the safety switch 124 indicates that the grinder door 120 is not in the closed configuration.

With further regard to safety, as illustrated in FIG. 1, the apparatus 100 may comprise a shield 126 which is positioned about the grinder 110 during operation thereof. The shield 126 may be configured to reduce noise emissions and/or prevent access to the grinder. With regard to reduction of noise emissions, as illustrated in FIG. 2, the shield 126 may comprise a liner 128 which is configured to absorb and/or reflect sound so as to reduce the amount of sound exiting through the shield. Accordingly, noise emissions encountered by an operator may be reduced. Further, the shield 126 may be configured to function as a blast shield which may protect the operator in the event that the grinder 110 experiences a mechanical malfunction.

As noted above, the grinder 110 may be configured to grind each of the seeds received therein to produce a powder comprising a plurality of seeds particles. As will be described below, grinding the seeds into seed particles may allow for testing of each of the ground seeds at the same time by taking advantage of the particle size. Accordingly, it may be desirable to grind the seeds such that the particles comprising the powder are below a threshold size. Thus, the apparatus 100 may comprise a screen 130 configured to regulate a maximum dimension of the seed particles exiting the grinder 110. The screen 130 may be configured to comprise openings which define the maximum dimension of the seed particles which travel therethrough. Accordingly, seeds may circulate and continue to be ground by the grinder 110 until the seed particles define a dimension which is smaller than the size of the openings. Thereby, the seed particles exiting the grinder 110 may be of relatively consistent dimensions which are below the maximum dimension as regulated by the screen 130.

Figure 4:
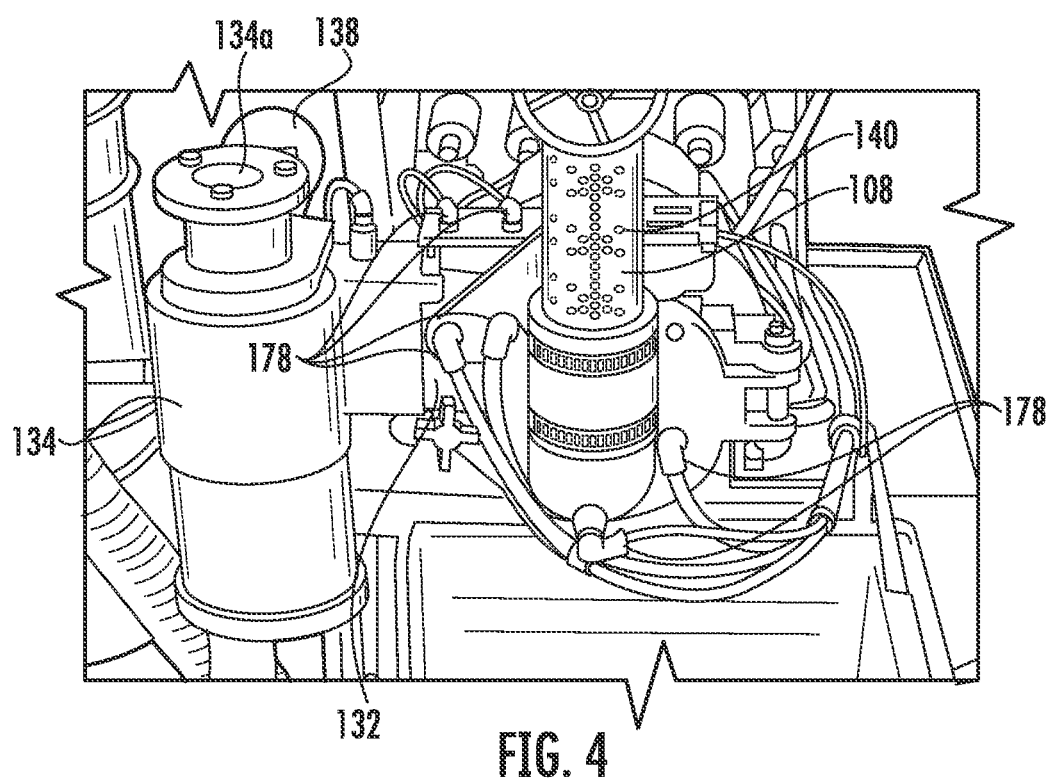
FIG. 4 illustrates an enlarged view of a cyclone separator of the apparatus of FIG. 1 in accordance with an example embodiment of the present invention.

After the seed particles comprising the powder exit the grinder 110 through the screen 130, the seed particles may be collected in a sample container. A sample container may in some embodiments directly couple to an outlet 132 of the grinder 110 to receive the powder. However, in the illustrated embodiment the apparatus 100 further comprises a cyclone separator 134. As illustrated in FIG. 4, the cyclone separator 134 may couple to the outlet 132 of the grinder 110 to receive the powder exiting therefrom. The cyclone separator 134 is configured to separate the seed particles comprising the powder from a fluid flow. In this regard, the cyclone separator 134 may comprise an air outlet 136 (see, e.g. FIG. 8) through which a fluid flow is directed. For example, as illustrated in FIG. 2, a suction hose 138 may couple to the air outlet 136 of the cyclone separator 134. The suction hose 138 may also couple to a vacuum source 139 (see, e.g. FIG. 1) which produces the flow of air through the apparatus 100. By pulling air through the grinder 110 and separating the particles from the flow of air with the cyclone separator 134, the seed particles may be more effectively removed from the grinder during operation.

In this regard, as illustrated in FIG. 4, the connecting tube 108 may comprise a plurality of inlet holes 140 through which air enters and travels into the grinder 110 as a result of the vacuum applied to the cyclone separator 134 by the vacuum source 139 through the suction hose 138. The fluid flow thereby travels from the connecting tube 108 through the grinder 110 and into the cyclone separator 134. The fluid flow may pick up seed particles and direct the seed particles through the screen 130 when they are small enough to travel therethrough. Accordingly, the fluid flow may carry therewith a plurality of seed particles when entering the cyclone separator 134. The cyclone separator 134 may direct the fluid flow so as to create a cyclone or vortex whereby the seed particles may tend to fall out of the fluid flow. Thereby a flow of relatively clean air may be directed through the air outlet 136 and suction hose 138 to the vacuum source 139 whereas the seed particles may fall downwardly.

Figure 5:
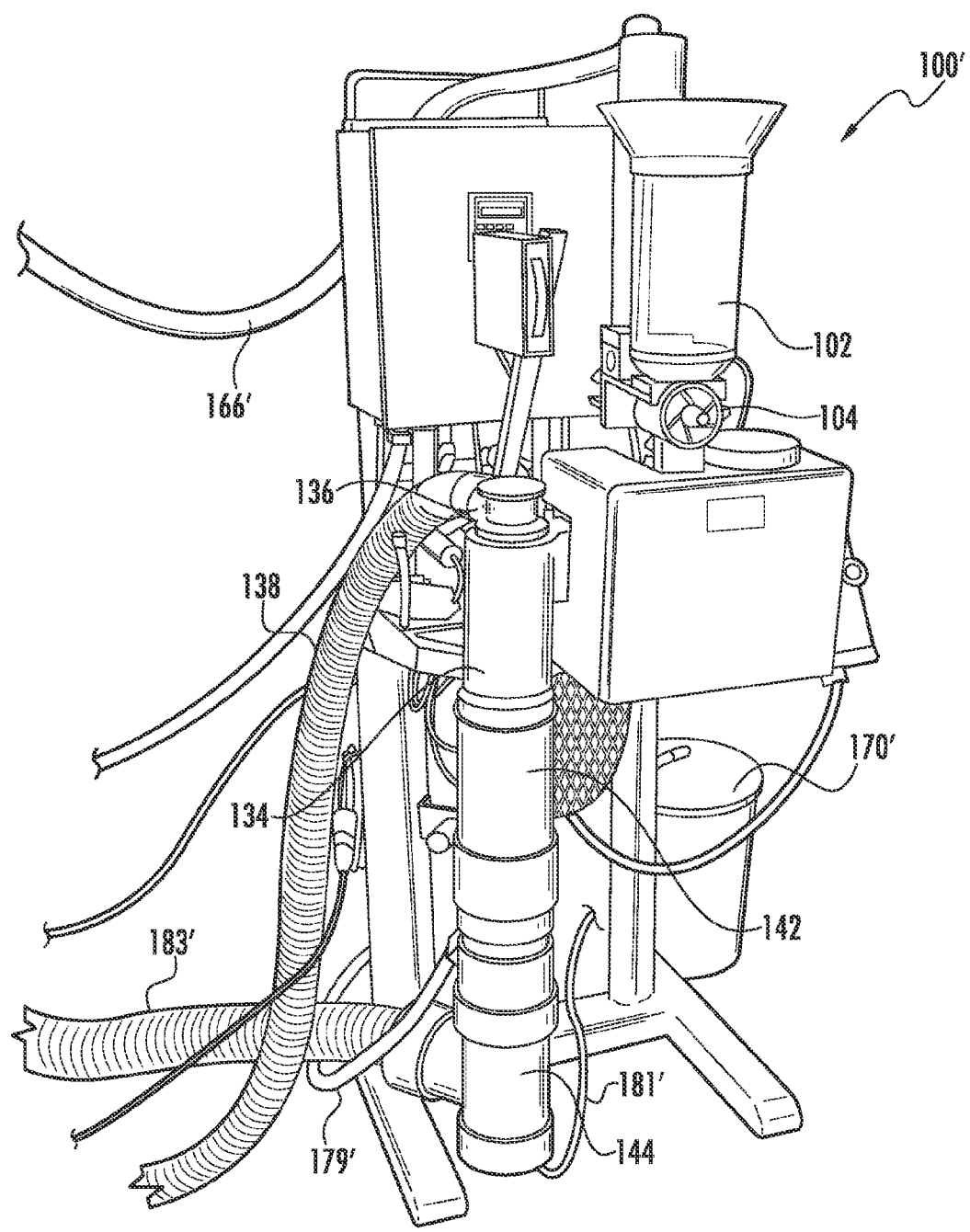
FIG. 5 illustrates a modified version of the apparatus of FIG. 1 with a remotely located neutral media source in accordance with an example embodiment of the present invention.

Accordingly, as illustrated in FIG. 5 (which illustrates a slightly modified embodiment of the apparatus 100', as will be discussed below), the cyclone separator 134 may be configured to couple to a sample container 142. The sample container 142 may thereby receive the seed particles which fall from the fluid flow. Accordingly, the seeds which initially enter the seed hopper 102 may ultimately be captured in the sample container 142 in the form of a powder comprising seed particles. The sample container 142 may be held in place so as to be coupled to the cyclone separator 134 by a support member 144. The support member 144 may be configured to translate on a track 146 (see, e.g. FIG. 1). In some embodiments the track 146 may comprise a pneumatic cylinder or other force producing means configured to move the sample container 142 so as to couple with the cyclone separator 134. Accordingly, the support member 144 may assist the sample container 142 in receiving the seed particles comprising the powder. Once all of the seeds have been metered into the grinder 110 by the seed metering device 104, and substantially all of the seed particles have exited the grinder, the support member 144 may lower on the track 146 so as allow the operator to retrieve the sample container 142.

Figure 6:
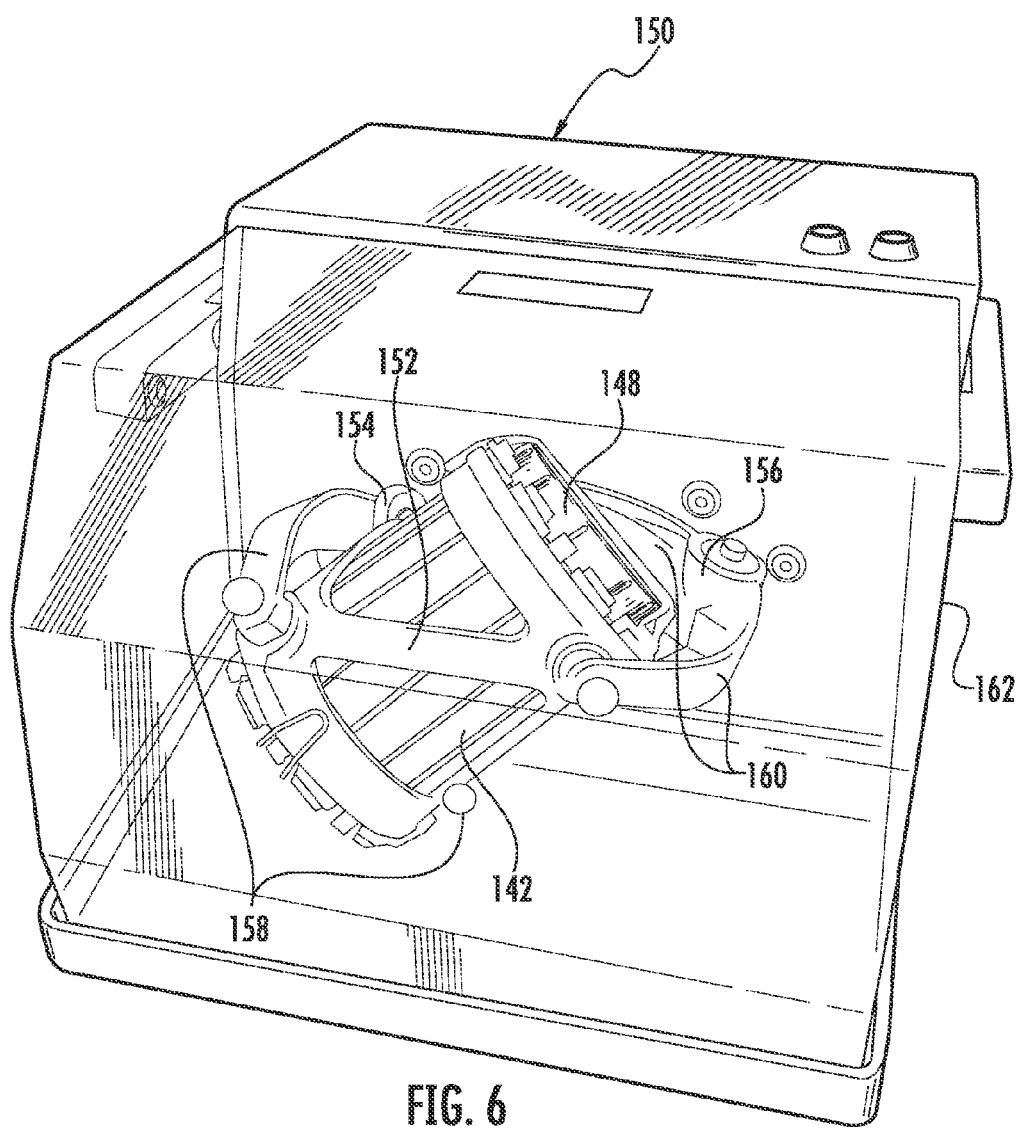
FIG. 6 illustrates a sample container in a mixing device in accordance with an example embodiment of the present invention.

As illustrated in FIG. 6, after the sample container 142 is retrieved, the operator may secure a lid 148 configured to seal the sample container. Thereafter, the powder comprising the plurality of seed particles may be mixed. In this regard, FIG. 6 further illustrates a mixing device 150 configured to mix the powder to obtain a substantially homogeneous distribution of the seed particles from the seeds within the powder. The mixing device 150 may comprise the TURBULA® Mixer-Shaker as sold by GLEN MILLS®, Inc. of Clifton, N.J. in some embodiments. The mixing device 150 may comprise a container holder 152 which is configured to receive and hold the sample container 142. First 154 and second 156 rotating members may each attach to opposite ends of the container holder 152 through unequal length arms 158, 160. When the rotating members 154, 156 rotate, the mixing device 150 may produce a tumbling effect as a result of the unequal length arms 158, 160. A protective lid 162 may be lowered when the mixing device 150 is in operation in order to prevent contact between the moving parts and the operator of the mixing device.

As described above, the mixing device 150 in the illustrated embodiment may be configured to mix the powder by tumbling the powder while the sample container 142 is sealed by the lid 148. Thus, for example, after the sample container 142 is removed from the cyclone separator 134, the lid 148 may be secured to the sample container, and then the sample container may be tumbled by the mixing device 150 without having to remove the powder from the sample container. Accordingly, the potential for contamination of the powder may be reduced. However, as may be understood by one having skill in the art, various embodiments of sample containers and corresponding mixing devices may be configured to mix the powder by tumbling or otherwise agitating the powder.

Once the powder is mixed, an operator may take a sample portion from the powder and conduct tests thereon. Due to the grinding of the seeds into a powder comprising a plurality of seed particles and mixing of the powder, the size of the sample portion needed to test each of the seeds may be less than the entirety of the powder produced from the seeds. In particular, the small size of the particles and the mixing thereof may produce a substantially homogeneous distribution of the particles such that even a relatively small sample portion may comprise at least one particle from each of the seeds which are ground.

Any of a variety of tests may be performed on the sample portion depending on what information is desired to be obtained from the sample. For example, in one embodiment the sample may be tested for presence of a GMO in the sample portion. Thus, a large quantity of seed product may be verified to be free of GMOs through testing of a relatively small number of seeds. However, as may be understood by one having skill in the art, various other tests may be conducted on the sample portion of the seed product.

As noted above, collecting and mixing the powder in the same sample container 142 may reduce the potential for cross-contamination. However, embodiments of the present invention may comprise additional features configured to reduce the probability of cross-contamination. In this regard, the apparatus 100 may comprise a cleaning system configured to introduce a neutral media to the grinder 110 to substantially prevent cross-contamination with a second plurality of seeds. The cleaning system may be distributed throughout various portions of the apparatus 100 in some embodiments.

For example, as illustrated in FIG. 1, a neutral media source 164 may be configured to introduce neutral media through a feed hose 166 into the seed hopper 102, which may then be metered into the grinder 110 using the metering device 104. Thus, the neutral media may be fed by gravity to the seed hopper 102 in some embodiments. In an alternate embodiment of the apparatus 100', as illustrated in FIG. 5, the neutral media may be stored in a remote location and directed to the seed hopper 102. Thereby, for example, a large quantity of the neutral media may be stored in a container at an alternate location, rather than positioned on top of the seed hopper 102, as illustrated in FIG. 1. When positioned remotely, the neutral media may be directed to the seed hopper 102 through a feed hose 166'. In one embodiment the neutral media may be agitated and directed through the feed hose 166' using a flow of compressed air.

Regardless of where the neutral media is stored, it may be directed to the seed hopper 102 (or directly to the grinder 110 in some embodiments). The neutral media may be configured to contact and remove any particles remaining from a plurality of seeds which have been processed by the apparatus 100. Thus, in some embodiments the neutral media may comprise a granulated plastic material. For example, the neutral media may comprise AERO-CLEAN® plastic blast media, as sold by MAXI-BLAST® Inc, of South Bend, Ind. Thus, after a first plurality of seeds are processed by the apparatus 100, the neutral media may be introduced into the seed hopper 102. The metering device 104 may then be operated so as to meter the seeds into the grinder 110. By depositing the neutral media into the seed hopper 102 and directing it through the metering device 104, the neutral media may contact and dislodge seed particles which may have been left by the first plurality of seeds as they traveled therethrough. Once the neutral media is introduced into the grinder 110, the neutral media may be ground by the grinder and the grinding operation may remove seed particles left behind by the seeds in the grinder.

However, in other embodiments the neutral media may comprise a plurality of control seeds which do not comprise a GMO. For example, this type of neutral media may be used when testing for the present of a GMO, as described above. By directing the control seeds through the seed hopper 102, the metering device 104, and the grinder 110, the control seeds may be ground and the resulting seed particles may fill in any gaps in the grinder and other depressions, holes and areas into which seed particles may deposit. Accordingly, the control seeds may deposit a barrier of known seed particles which may further assist in preventing cross-contamination with a second plurality of seeds which are processed after a first plurality of seeds. In some embodiments the operation of grinding the control seeds may be conducted prior to grinding the seeds of the first plurality of seeds. For example, the control seeds may be directed through the apparatus 100 as an initial matter before processing any seeds for testing purposes. However, in other embodiments the control seeds may be ground between processing of a first plurality of seeds and a second plurality of seeds, as described above with respect to use of a neutral media comprising plastic.

Figure 7:
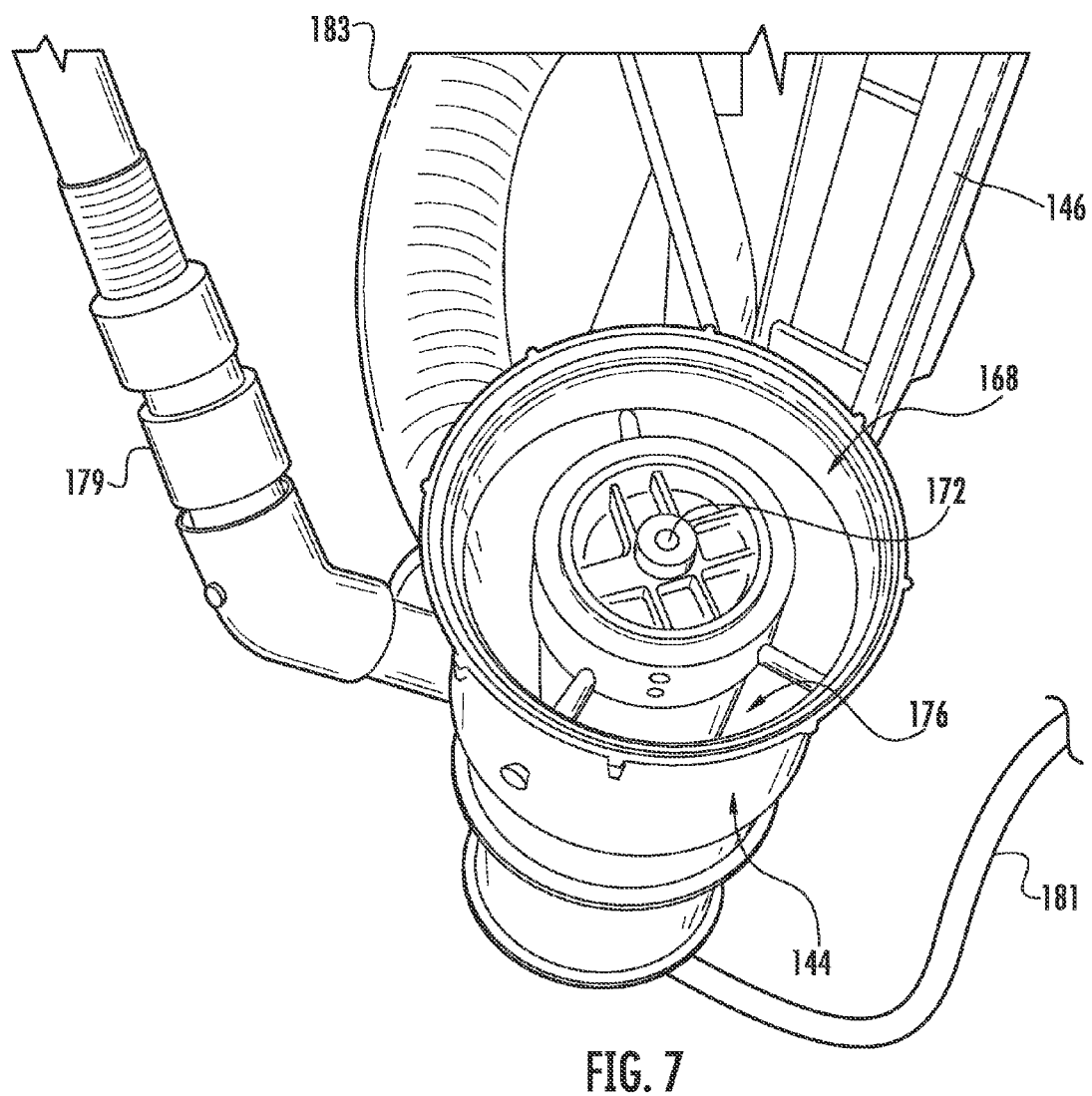
FIG. 7 illustrates an enlarged view of a support member of the apparatus of FIG. 1 in accordance with an example embodiment of the present invention.

Additionally or alternatively, the cleaning system may be configured to project a cleaning mixture into the cyclone separator 134 to clean the cyclone separator. The cleaning mixture may comprise the neutral media in some embodiments. Therefore, for example, the cleaning mixture may comprise granulated plastic in some embodiments. As illustrated in FIG. 7, in order to project the cleaning mixture into the cyclone separator 134, the cleaning system may comprise a blasting device 168. The blasting device 168 may receive the cleaning mixture from a separate cleaning mixture source 170 (see FIG. 1), 170' (see FIG. 5), or the neutral media source 164 in some embodiments. The cleaning mixture may be delivered to the cyclone separator 134 via a feed hose 179 (see FIG. 1), 179' (see FIG. 5) via a gravity feed or via agitation and a flow of compressed air as described above with respect to the feed hose 166, 166' employed to deliver neutral media to the seed hopper 102.

As illustrated, the blasting device 168 may be integral with the support member 144. Thus, in order to clean the cyclone separator 134, the support member may raise into contact with the cyclone separator using the track 146. Thereby the blasting device 168 may project the cleaning mixture from an outlet 172 directly into the cyclone separator 134. For example, the blasting device 168 may project the cleaning mixture using pressurized air. In particular, the feed hose 179, 179' may direct a supply of the cleaning mixture into the center of the blasting device 168, and an air hose 181 (see FIG. 1), 181' (see FIG. 5) may project the cleaning mixture 134 through the outlet 172 into the cyclone separator 134. For example, the air hose 181, 181' may enter through the bottom of the blasting device 168, and curl downwardly such that an outlet of the air hose is directed downwardly at a surface covered by the cleaning mixture. Thereby, when the air hose 181, 181' directed air into the blasting device 168, the cleaning mixture is propelled through the outlet 172 into the cyclone separator 134.

As illustrated in FIG. 4, the cyclone separator 134 may comprise a viewing lens 134a which may be used by an operator to ensure that the cleaning mixture has sufficiently removed seed particles from the cyclone separator. In some embodiments the cleaning system may further comprise a vacuum source 174, as illustrated in FIG. 1. Thus, the cleaning mixture and any particles from the seeds which are removed from the cyclone separator 134 may be sucked through an inlet 176 (see FIG. 8) in the support member 144 and out of the apparatus 100 through a vacuum hose 183 (see FIG. 1), 183' (see FIG. 5) by the vacuum source 174.

The cleaning system may further comprise one or more air jets 178 (see, e.g. FIGS. 3, 4, and 8) configured to direct a pressurized flow of air into the grinder 110 to clean the grinder. FIG. 3 illustrates air jets 178 which direct the pressurized flow of air into the outlet 132 of the grinder 110. Further, as illustrated in FIGS. 4 and 8, the air jets 178 may direct the pressurized air into the grinder 110 from the front, back, and top as well as from various other angles as may be understood by one having skill in the art. Thus, the pressurized air may be directed into the grinder 110 to remove any remaining seed particles. For example, the air jets 178 may direct the pressurized air into the grinder 110 before, during and/or after the neutral media is ground by the grinder. Further, the inlet 176 in the support member 144 may be used to suck out any of the seed particles which are removed from the grinder 110 by the pressurized air emitted from the air jets 178. Thus, the various portions of the cleaning system may work in conjunction to prevent cross-contamination.

In some embodiments the cleaning system may further comprise a negative air flow system configured to direct an ambient air flow generally down and away from the grinder 110 as well as other parts of the apparatus 100. Accordingly, any seed particles which may enter the air around the apparatus 100 may be removed so as to avoid contamination of the powder prior to installation of the lid 148 on the sample container 142. As a further cross-contamination measure, the sample container 142 may be configured to store the seeds before the seeds are ground into the powder. In this regard, the sample container 142 may serve to initially store the seeds, receive the powder resulting from grinding the seeds, and mix the powder therein. Therefore, the potential for cross-contamination between successive pluralities of seeds which are ground may be reduced.

Accordingly, embodiments of the apparatus 100 as described above may produce powder from seeds which may be used for testing purposes, for example. Further, embodiments of related methods are also provided herein. In this regard, FIG. 9 illustrates an embodiment of a method for high throughput simultaneous sampling of a plurality of seeds. As illustrated, the method may comprise receiving a first plurality of seeds in a hopper at operation 200. Further, the method may include metering the first plurality of seeds into a grinder at operation 202. Additionally, the method may include grinding each of the seeds of the first plurality of seeds in the grinder to produce a powder comprising a plurality of seed particles at operation 204. Also, the method may include collecting the powder in a sample container at operation 206. The method may further include selecting a sample portion of the powder for testing at operation 208. At operation 210 the method may additionally include distributing a neutral media into the grinder. The method may also include grinding the neutral media to substantially prevent cross-contamination with a second plurality of seeds at operation 212.

In some embodiments the method may additionally or alternatively comprise other operations including those operations illustrated in dashed lines in FIG. 9. For example, the method may further comprise regulating a maximum dimension of the seed particles exiting the grinder at operation 214. Additionally, the method may comprise directing a fluid flow through the grinder while grinding the seeds at operation 216. The method may also comprise separating the seed particles from the fluid flow using a cyclone separator at operation 218. Further, the method may comprise sealing the sample container at operation 220 and mixing the powder in the sample container at operation 222. Also, as indicated at operation 224, mixing the powder may comprise tumbling the sample container. Thereby, as indicated at operation 226, the method may include mixing the powder to obtain a substantially homogeneous distribution of the seed particles from the seeds within the powder. Further, the method may include testing for presence of a GMO in the sample portion at operation 228.

The method may additionally include directing an ambient air flow generally down and away from the grinder at operation 230. Also, the method may include projecting a cleaning mixture into the cyclone separator to clean the cyclone separator at operation 232. Further, the method may include directing a pressurized flow of air into the grinder to clean the grinder at operation 234. Accordingly, various embodiments of methods of high throughput simultaneous sampling of a plurality of seeds are provided. Theses methods may be configured to reduce the probability of cross-contamination.

Many modifications and other embodiments of the invention set forth herein will come to mind to one skilled in the art to which these invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for high throughput simultaneous sampling of a plurality of seeds, comprising:
   receiving a first plurality of seeds in a hopper;
   metering the first plurality of seeds into a grinder;
   grinding each of the seeds of the first plurality of seeds in the grinder to produce a powder comprising a plurality of seed particles;
   collecting the powder in a sample container;
   selecting a sample portion of the powder for testing;
   distributing a neutral media into the grinder; and
   grinding the neutral media to substantially prevent cross-contamination with a second plurality of seeds.

2. The method of claim 1, further comprising regulating a maximum dimension of the seed particles exiting the grinder.

3. The method of claim 1, further comprising mixing the powder to obtain a substantially homogeneous distribution of the seed particles from the seeds within the powder.

4. The method of claim 3 further comprising:
   sealing the sample container; and
   mixing the powder in the sample container.

5. The method of claim 4, further comprising tumbling the sample container.

6. The method of claim 1, further comprising directing a fluid flow through the grinder while grinding the seeds; and
   separating the seed particles from the fluid flow using a cyclone separator.

7. The method of claim 1, further comprising projecting a cleaning mixture into the cyclone separator to clean the cyclone separator.

8. The method of claim 7, wherein the cleaning mixture comprises the neutral media.

9. The method of claim 1, further comprising directing an ambient air flow generally down and away from the grinder.

10. The method of claim 1, further comprising directing a pressurized flow of air into the grinder to clean the grinder.

11. The method of claim 1 further comprising testing for presence of a genetically modified organism in the sample portion.

12. The method of claim 1, wherein the neutral media comprises a granulated plastic material.

13. The method of claim 1, wherein the neutral media comprises a plurality of control seeds which do not comprise a genetically modified organism.

14. The method of claim 13, wherein grinding the neutral media is conducted prior to grinding the seeds of the first plurality of seeds.

* * * * *